United States Patent [19]

De Jonge et al.

[11] Patent Number: 4,980,504
[45] Date of Patent: Dec. 25, 1990

[54] AROMATIC AMIDE GROUPS-CONTAINING DIAMINES AND POLYMERS PREPARED THEREFROM

[75] Inventors: Cornelis R. H. I. De Jonge, Giesbeek; Gerrit Hoentjen, Westervoort; Theodorus J. Bouwmans, Duiven, all of Netherlands

[73] Assignee: Akzo N.V., Netherlands

[21] Appl. No.: 387,201

[22] Filed: Jul. 28, 1989

[30] Foreign Application Priority Data

Aug. 1, 1988 [NL] Netherlands .................. 8801915

[51] Int. Cl.$^5$ ........................................ C07C 233/77
[52] U.S. Cl. ............................ 564/156; 528/310; 528/350; 528/353
[58] Field of Search ................................ 564/156

[56] References Cited

U.S. PATENT DOCUMENTS

| | | | |
|---|---|---|---|
| 3,049,518 | 8/1962 | Stephens et al. | 528/348 |
| 3,193,579 | 7/1965 | Goldberg et al. | 564/156 |
| 4,326,076 | 4/1982 | Moniot et al. | 564/156 |

OTHER PUBLICATIONS

M. Bruma & G. Neamtu, Poly-1,2,4-Oxadiazoles, IX Ordered Poly-1,3,4-Oxadiazole-Amide-Imides, Revenue Roumaine de Chimie, 26, pp. 87-93 (1981).
V. A. Gusinskaya et al., Poly (Amido) Imides Based on Symmetrical and Asymmetrical Imido Acid Dichlorides, High Polymers Institute, U.S.S.R. Academy of Sciences, pp. 3062-3068 (1976).
Yamakazi et al., Studies on Reactions of the N-Phosphonium Salts of Pyridines, XIV, Wholly Aromatic Polyamides by the Direct Polycondensation Reaction by Using Phosphites in the Presence of Metal Salts, J. Pol. Sci, 13, pp. 1373-1380 (1975).
G. Neamtu et al., High-Temperature Polymers Polybenzothiazole-Amide-Imides, pp. 29-38 (1981).
Kirk-Othmer, Encyclopedia of Chemical Technology, 3rd ed., vol. 3, pp. 229-237 (1978).

*Primary Examiner*—Glennon H. Hollrah
*Attorney, Agent, or Firm*—David H. Vickrey; Louis A. Morris

[57] ABSTRACT

Diamines having a 1,1,3-trimethylphenylindane dicarboxylic moiety linked on both sides to phenylene diamine by an amide bond (PIDA diamines) are disclosed. By reacting these diamines with aromatic difunctional acid derivatives, amorphous polymers having high glass transition temperatures (Tg) can be prepared. If aliphatic diacid derivatives are used the resulting polymers have a lower Tg, but have the advantage of melt-processability. The PIDA-diamines can also be used in the preparation of polyimides, being reacted either with tri- or tetracarboxylic anhydrides or with imide group-containing acid derivatives.

1 Claim, No Drawings

AROMATIC AMIDE GROUPS-CONTAINING DIAMINES AND POLYMERS PREPARED THEREFROM

BACKGROUND OF THE INVENTION

The invention relates to a novel diamine containing amide groups and polyamides and polyimides based on such diamine. The polyamides of the current invention are formed by the polycondensation of the novel diamine with dicarboxylic acid or a derivative thereof.

A diamine which contains aromatic amide groups and may be used as a raw material in the preparation of polyamides is known from U.S. Pat. No. 3,049,518. The diamine described in U.S. Pat. No. 3,049,518 is N,N'-bis(3-aminophenyl)-isophthalamide. Its reaction with difunctional acid derivatives generates crystalline polymers. They form a class of polymers different from the amorphous polyamides generated from diamines according to the invention.

The polycondensation of 2,5-bis(p-aminophenyl)-1,3,4oxadiazole with one of the following two diacid chlorides

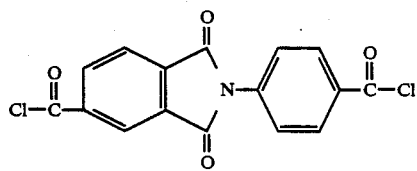

(1)

or

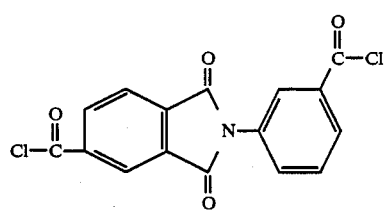

(2)

is known from "Poly-1,3,4-Oxadiazoles. IX Ordered Poly-1,3,4-Oxadiazole-Amide-Imides", Maria Bruma and Gabriele Neamtui *Revenue Roumaine de Chimie*, 26, 87–93 (1981).

SUMMARY OF THE INVENTION

The current invention discloses a diamine of the formula

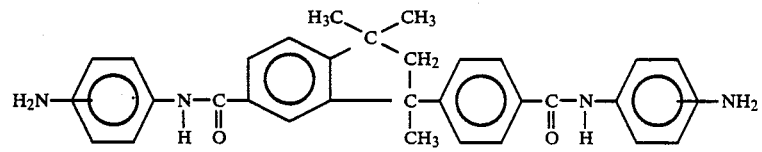

The diamine may be polycondensed with a dicarboxylic acid or a derivative thereof to produce a polyamide.

The diamine may also be used to produce a polyimide.

DETAILED DESCRIPTION OF THE INVENTION

The invention relates to diamines of the formula

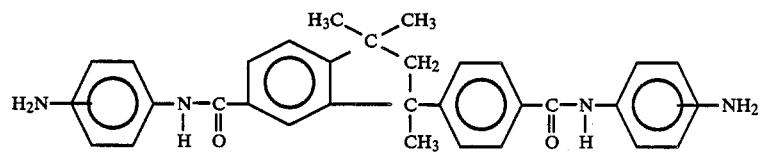

The invention also relates to polyamides and polyimides based on these diamines. Because of the asymmetrical structure of 1,1,3-trimethyl-3-phenylindane-4',5-dicarboxylic acid (PIDA) in the diamines according to the invention such polymers display little tendency to crystallize.

Compounds in which the amino groups are in the para position relative to the amide groups will be referred to hereinafter as para-PIDA diamines. The same applies to meta-PIDA and ortho-PIDA diamines.

A major advantage of the diamines according to the invention is the possibility of preparing amorphous polymers having a relatively high glass transition temperature (Tg).

Polymers having a relatively high Tg are formed by reacting a diamine according to the invention with aromatic difunctional acid derivatives. Such polymers are especially suited to be used in the electronics industry, since in this industry resistance to a brief high thermal load (soldering) is often required. In the aircraft industry there also is a great demand for polymers having a high Tg.

A drawback to high Tg polymers is that they can be melt processed only with difficulty or not at all. This is caused on the one hand by the difference between decomposition temperature and processing temperature being too small and on the other by the commonly used processing equipment as a rule not being operable at temperatures above 400° C. If the diamines according to the invention are polycondensed with aliphatic difunctional acid derivatives or mixtures of aliphatic and aromatic difunctional acid derivatives, polymers having a Tg up to about 280.C are obtained. Thus, the invention also provides polymers that may be melt processed by conventional techniques, such as moulding, injection moulding, and extrusion, even though a lower Tg will have to be accepted then.

The invention also permits preparing copolymers in which the diamines according to the invention are replaced in part with other diamines of an aliphatic or aromatic structure or in which mixtures of diacids or diacid chlorides are employed.

Alternatively, the diamines according to the invention may be polymerized with cyclic anhydrides of tetracarboxylic acids, such as pyromellitic acid and benzophenone tetracarboxylic acid. Such a process generates a polyamic acid from which a polyimide may be formed using ring closure. Of course, this may also be achieved using tricarboxylic anhydrides. The process of casting a polyamic acid film which is subsequently cured with imide forming is known to the person skilled in the art. The polyamic acids formed by using diamines according to the invention are amorphous and may consequently be processed from a solution into products, such as films, by conversion into polyimides.

The diamines according to the invention are also suited to be used for preparing polyamidimides by reaction with a dicarboxylic acid derivative in which a preformed imide structure is present. Such imide monomers and polyimides prepared therewith are described in Vysokomol soyed.A18:No. 12, 2681–2686 (1976).

The preparative process is particularly advantageous in that it presents voids and cracks in the polymer surface.

By reaction steps known in themselves the diamines according to the invention may be prepared from phenylindane dicarboxylic acid (PIDA) or phenylindane dicarboxylic acid chloride (PIDA-Cl) and o-, m- or p-nitroaniline. The resulting dinitro compound may be reduced to the diamine in a known manner.

The preparation of the polyamides according to the invention may be carried out in a manner analogous to the one described for the known polyamides in Kirk-Othmer, Encyclopedia of Chemical Technology, 3rd ed. Vol. 3, pp. 229–237 (1978).

In the preparation on a laboratory scale use may be made of a method described by Yamazaki et al. in J. Pol. Sci. 13 (1975) pp. 1373–1380. For preparation on an industrial scale preference is generally given to interfacial polymerization or polymerization from the solution. These types of polymerization are known in the art and need no further elucidation here.

The invention will be further described in, but not limited by the following examples.

EXAMPLES

Example 1

Preparation

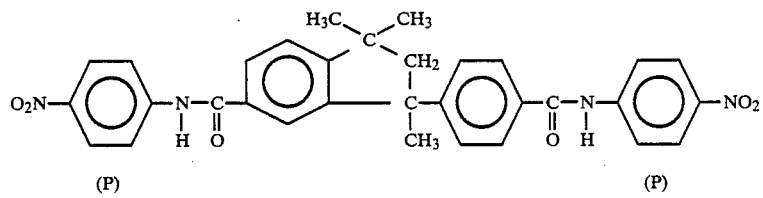

(P)

Method A:
from diacid +p-nitroaniline in conformity with the so-called Yamazaki method.

Procedure

Weighed into a 3-1 three-necked flask fitted with a contact thermometer, a stirrer, a heating device, an $N_2$ apparatus, a reflux condenser, and a bubble gauge are:

162.2 g of phenylindane dicarboxylic acid $M \approx 324.4 \approx 0.50$ moles
+140.0 g of p-nitroaniline $M = 138.1 \approx 1.01$ moles
+340 g of triphenyl phosphite $M = 310.3 \approx 1.10$ moles (9.6% excess)
+1000 ml of N-methyl pyrrolidone (NMP)
+750 ml of pyridine
+115 g of lithium chloride.

In a nitrogen atmosphere the entire content of the flask dissolve almost immediately, with brownish black discoloration The flask and its contents are heated to 85°–90° C., with stirring. After about 15 minutes a solid is formed. The flask's contents are stirred for in all 3 hours at the aforesaid temperature to complete the reaction. Next, the reaction mixture is cooled to room temperature, 1 l of methanol is added dropwise, and the whole is finally precipitated in 25 l of water, with stirring. After the addition has been completed, there remains a brown, viscous precipitate. The mother liquor is decanted and the remaining viscous precipitate is mixed, with stirring, with 1 l of methanol. The viscous mass crystallizes out to form a beige solid. Following filtration in vacuo, re-washing and re-filtration the solid is dried in vacuo. The solid is first dried for 16 hours at 50° C. in a vacuum of 12 mmHg, and subsequently for 11 hours at 80° C. in a vacuum of 0.1 mmHg. After drying to a constant weight there remained 236.4 of a sandy-dark beige solid with a melting range of 158.5°–165° C. The yield is 84%.

Method B:
from diacid chloride +p-nitroaniline

Procedure

Weighed into a 1-1 flanged flask fitter with a thermometer, a stirrer, an $N_2$ apparatus, and a bubble gauge are:

9.60 g of phenylindane diacid chloride $M = 361.3 \approx 26.6$ mmoles
+7.73 g of p-nitroaniline $M = 138.1 \approx 56$ mmoles
+200 ml of N-methyl pyrrolidone (dried on molecular sieves 3Å).

The dark brown solution is stirred in an $N_2$ atmosphere at room temperature, the diacid chloride slowly dissolving. After having been stirred for 16 hours, the solution (including the dissolved diacid chloride) is poured into water, with stirring. The resulting precipitate, a yellowish white solid, is washed with water several times, filtered off, and finally dried for 16 hours at 85° C./12 mmHg, followed by drying at 85° C./0.1 mmHg for 7 hours, until a constant weight is obtained.

Obtained are 14.44 g of product.
Color: yellowish beige.
Yield: 96.3%.
Melting range: 162.2.–167.9° C.

Example 2

Preparation

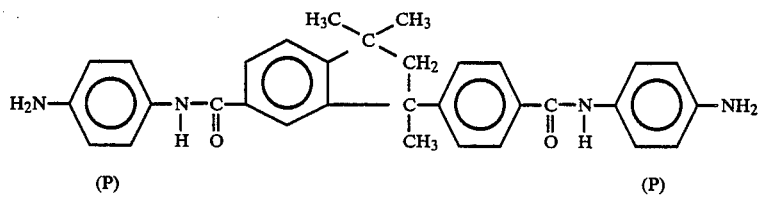

(P) ... (P)

Reduction of dinitro to the corresponding diamino compound.

Procedure

Into a 2-1 steel high-pressure autoclave with lifting device (manufactured by Hofer) are introduced:
236 g of dinitro compound M=564≈0.42 mmoles
+11.8 of 50% of Raney nickel suspension
+1200 ml of dimethyl acetamide (DMA), dried on molecular sieves 4 Å.

After being evacuated three times and subsequently flushed with $N_2$, the autoclave is brought under an $H_2$ atmosphere at an atmospheric pressure of 40–45. The reaction takes place at 80°–90° C. Upon its completion there remains a blackish brown solution. The catalyst remainders are filtered off over infusorial earth and at reduced pressure. The remaining DMA solution is precipitated in 4 l of $H_2O$ with stirring. In the process a finely divided pale beige precipitate is formed. After it has been filtered, the solid is again agitated and filtered off 3 times. Finally, the reaction product is dried until the weight is constant, viz. for 16 hours/70° C./13 mmHg, followed by 16 hours/75° C./1 mmHg. Obtained are 197.4 g of product. The yield is 93.6%. The beige solid has a melting range of 231.6°–234° C.

Example 3

Preparation by the Yamazaki Method of Composite Polyamides From a Diacid With a Diamine According to the Invention

Procedure

Weighed into a 250-ml three-necked flask fitted with a contact thermometer, a reflux condenser with bubble gauge, a stirrer, an $N_2$ apparatus, and a heating device are:
10.08 g of para-PIDA diamine M=504≈0.02 moles
+4.32 g of 2.6-naphthalene dicarboxylic acid M=216.2≈0.02 moles
+40 ml of N-methyl pyrrolidone (NMP)
+30 ml of pyridine
+2.8 g of lithium chloride
+16 g of triphenyl phosphite M=310.3≈0.05 moles. Slight excess.

After it has been flushed with $N_2$, the flask with its contents is heated to 85°–90° C. After 30 minutes a lightly colored precipitate is formed in the solution, which up to then has been a clear dark brownish green. Also the viscosity of the flask's contents increases. After 3 hours the reaction is stopped and the whole cooled down. The contents of the flask are diluted with 100 ml of DMA. The solution, which is clear now, is precipitated in 1.3 l of methanol, with stirring. The sandy polymer precipitate is after-flushed with methanol on a filter several times. Next the polymer is dried for 16 hours/65° C./12 mmHg, followed by 7 hours at 80°→100° C./0.3 mmHg, until a constant weight is obtained. After drying a sandy polymer is left.
Weight: 13.51 g.

The yield is: 98.8%.
The relative viscosity is 1.40.
Data on other polyamides prepared in conformity with this general specification are in Table 1. Abbreviations used in this Table are:
TGA: thermographic analysis
DSC: differential scanning calorimetry.

The relative viscosity was determined as follows:
A 0.50% solution of the appropriate polymer in dimethyl acetamide (DMA) with 5% of lithium chloride is prepared and filtered.
The efflux times of both the solvent and the solution are measured under the same conditions in an Ubbelohde viscometer at 25.0° C.

$$\eta_{rel} = \frac{\text{efflux time of polymer solution}}{\text{efflux time of solvent}}$$

Both in the aforesaid case and for the polyamides in the table $\eta_{rel}$ was measured each time in a 0.50% solution.

Example 4

Preparation of Polyamic Acid

Into a 500-ml three-necked flask fitted with a reflux condenser, a thermometer, a stirrer, an inlet tube for nitrogen, and powder metering funnel are introduced: 25.5 g of para-PIDA diamine (0.05 moles) and 250 ml of dimethyl acetamide (DMAc), dried on molecular sieves 3 Å. The diamine is dissolved with stirring to form a clear, brown solution. Next, 16 g of solid benzophenone dianhydride (0.05 moles) are slowly added through the powder metering funnel. The temperature is prevented from rising too high by simultaneous cooling ($T$max=26° C). During the addition there is an increase in viscosity as a result of polyamic acid being formed. Upon completion of the reaction the solution is diluted with an additional 100 ml of DMAc. The viscosity of the resulting clear brown solution is measured with an Ubbelohde viscometer at 25.0° C. The inherent viscosity is 0.54.

Example 5

Preparation of Polyimide from Polyamic Acid 30 ml of the aforementioned polymer solution is subsequently poured onto a heatable horizontally positioned glass plate (20×12 cm). Barring dust, the solvent is then evaporated at 55°–60° C. After 4–6 hours a pale yellow, fully transparent film remains. After the glass plate has been removed, the flexible film is clamped into a tenter frame on all four sides. The whole is placed in a forced circulation air oven and then subjected to the following temperature cycle:
30 minutes at 60° C.

30 minutes at 90° C.
30 minutes at 120° C.
30 minutes at 140° C.
30 minutes at 160° C.
30 minutes at 180° C.
30 minutes at 210° C.
30 minutes at 240° C.

Up to about 140° C., most of the remaining solvent evaporates. Higher temperatures are attended with cyclization and water being split off. After having been subjected to the aforementioned temperature cycle, the resulting clear yellow film has a glass transition temperature (Tg) of 265° C. and a decomposition temperature of 405° C., both determined by D.S.C.

Example 6

Polyimide Based on Imido Acid Chlorides and Meta-PIDA Diamine

Acid chlorides in which an imide structure is already present may be prepared as described by Bruma and Neamtu in *Revue Roumaine de Chimie*, 26 87–93 (1981). Using diamines according to the invention this method permits the preparation of polyimides as described hereinafter for meta-PIDA diamine In a three-necked flask, 20.88 g of meta-PIDA diamine (0.0414 moles) are dissolved in 150 ml of N-methyl pyrrolidone (NMP). Using an ice bath the whole is cooled down to 2° C. and 14.4 g (0.0414 moles) of N-(4-carbonyl chloride phenyl)-4-carbonyl chloride phthalimide are added. The temperature increases to 24 ° C. despite cooling.

The resulting solution is clear and highly viscous. After 2 hours 600 ml of NMP are added and the whole is precipitated in 3 l of methanol. Pale yellow fibers are formed. Following filtration, washing, and drying there are left 32.36 g (95.8%) of polymer For data on the prepared polyimides see Table 2.

TABLE 1

| POLYAMIDES | | Pol. Method | Yield (%) | TGA Wt. loss 0% (°C.) | TGA Wt. loss 10% (°C.) | DSC Tg (°C.) | DSC Td (°C.) | Relative visc. in DMA/LiCl (0,5%) $\eta_{rel}$ |
|---|---|---|---|---|---|---|---|---|
| Diamine | Diacid | | | | | | | |
| meta-PIDA | $-\overset{O}{\overset{\|}{C}}(CH_2)_4\overset{O}{\overset{\|}{C}}-$ | yamazaki | Quant. | 325 | 405 | 235 | 305 | 1.49 |
| meta-PIDA | $-\overset{O}{\overset{\|}{C}}(CH_2)_7\overset{O}{\overset{\|}{C}}-$ | " | " | 330 | 405 | 205 | 300 | 1.49 |
| meta-PIDA | $-\overset{O}{\overset{\|}{C}}(CH_2)_{10}\overset{O}{\overset{\|}{C}}-$ | " | " | 340 | 415 | 195 | 330 | 1.80 |
| meta-PIDA | $-\overset{O}{\overset{\|}{C}}-C_6H_4-\overset{O}{\overset{\|}{C}}-N(H)(CH_2)_3N(H)-\overset{O}{\overset{\|}{C}}-C_6H_4-\overset{O}{\overset{\|}{C}}-$ | " | " | — | — | 275 | 380 | 1.50 |
| meta-PIDA | meta-phenylene diacid | " | " | 385 | 470 | 285 | 375 | 1.51 |
| meta-PIDA | meta-phenylene diacid | " | " | 365 | 470 | 310 | 380 | 1.76 |
| meta-PIDA | indane-based diacid | " | " | 385 | 480 | 300 | | 1.20 |
| meta-PIDA | 2,6-naphthalene diacid | " | " | 365 | 480 | 295 | 380 | 1.45 |

TABLE 1-continued

| POLYAMIDES | | Pol. Method | Yield (%) | TGA Wt. loss 0% (°C.) | TGA Wt. loss 10% (°C.) | DSC Tg (°C.) | DSC Td (°C.) | Relative visc. in DMA/LiCl (0,5%) $\eta_{rel}$ |
|---|---|---|---|---|---|---|---|---|
| Diamine | Diacid | | | | | | | |
| para-PIDA | $-\overset{O}{\underset{\|}{C}}(CH_2)_4\overset{O}{\underset{\|}{C}}-$ | " | " | 305 | 400 | 250 | 315 | 1.26 |
| para-PIDA | $-\overset{O}{\underset{\|}{C}}(CH_2)_{10}\overset{O}{\underset{\|}{C}}-$ | " | " | 310 | 425 | 230 | 310 | 1.32 |
| para-PIDA | (m-phenylene dicarbonyl) | " | " | 405 | 490 | 295 | 390 | 1.22 |
| para-PIDA | (p-phenylene dicarbonyl) | " | " | 395 | 475 | 350 | 410 | 1.22 |
| para-PIDA | (indane dicarbonyl) | " | " | 410 | 480 | 345 | 410 | 1.24 |
| para-PIDA | (2,6-naphthalene dicarbonyl) | " | " | 405 | 480 | 350 | 405 | 1.40 |

TABLE 2

| POLYAMIDES | | Yield % | TGA Weight loss 0% (°C.) | TGA Weight loss 10% (°C.) | DSC Tg (°C.) | DSC Td (°C.) | Relative Visc. 0.5% pol. in DMA/LiC $\eta_{rel}$ |
|---|---|---|---|---|---|---|---|
| Diamine | Diacid Chloride | | | | | | |
| metal-PIDA | (4-carbonyl-phenyl-phthalimide) | 95.8 | 400 | 475 | 310 | 380 | 1.76 |
| para-PIDA | " | 98.2 | 415 | 495 | 370 | — | 2.06 |
| meta-PIDA | (3-carbonyl-phenyl-phthalimide) | 97.7 | 400 | 493 | 300 | — | 1.43 |
| para-PIDA | " | 95.5 | 395 | 465 | 320 | 400 | 1.98 |

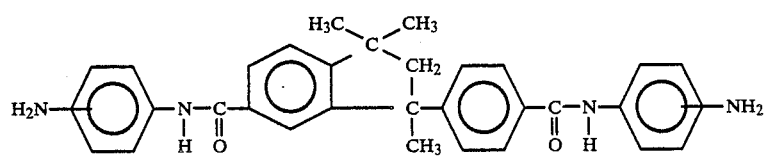

We claim:
1. A diamine of the formula